United States Patent [19]

Mattson

[11] Patent Number: 4,785,796
[45] Date of Patent: Nov. 22, 1988

[54] OTOSCOPE AND FLEXIBLE, DISPOSABLE CURETTE FOR USE THEREWITH

[76] Inventor: Philip D. Mattson, 1776 Plantation Way, El Cajon, Calif. 92020

[21] Appl. No.: 907,190

[22] Filed: Sep. 12, 1986

[51] Int. Cl.⁴ .................. A61B 1/22; A61B 17/22; F21V 33/00
[52] U.S. Cl. ................................ 128/9; 128/304; 128/23; 362/109
[58] Field of Search ............ 128/4, 6, 7, 9, 10, 128/11, 15, 16, 304, 784, 759, 23; 362/32, 109; 433/29

[56] References Cited

U.S. PATENT DOCUMENTS

| 622,389 | 4/1899 | Peery | 128/304 |
|---|---|---|---|
| 1,533,123 | 4/1925 | Lewis | 128/304 |
| 1,556,510 | 10/1925 | King | 128/23 |
| 1,737,106 | 11/1929 | Campbell et al. | 128/304 |
| 2,331,732 | 10/1943 | Ryzmek | 128/304 |
| 2,885,537 | 5/1959 | Wood | 128/11 |
| 3,110,304 | 11/1963 | Hartman | 128/304 |
| 3,195,536 | 7/1965 | Hovnanian et al. | 128/16 |
| 3,254,356 | 6/1966 | Yao et al. | 128/304 |
| 3,592,186 | 7/1971 | Oster | 128/304 |
| 3,626,946 | 12/1971 | Messey | 128/304 |
| 3,635,222 | 1/1972 | Robinson | 128/304 |
| 4,027,658 | 6/1977 | Marshall | 128/304 |
| 4,566,439 | 1/1986 | Burgin | 128/6 |
| 4,572,180 | 2/1986 | Deenadayalu | 128/304 |
| 4,638,792 | 1/1987 | Burgin | 128/6 |

FOREIGN PATENT DOCUMENTS

| 2566668 | 1/1986 | France | 128/9 |
|---|---|---|---|
| 178945 | 6/1966 | U.S.S.R. | 128/9 |
| 253997 | 7/1970 | U.S.S.R. | 128/11 |
| 1435600 | 5/1976 | United Kingdom | 128/16 |

Primary Examiner—Richard C. Pinkham
Assistant Examiner—Mark S. Graham
Attorney, Agent, or Firm—Beveridge, DeGrandi & Weilacher

[57] ABSTRACT

An otoscope having a coupling device and a curette having a corresponding coupling device for releasably attaching the curette to the otoscope are useful for examining and treating small cavities such as the ear canal. The otoscope includes a lens for viewing the ear canal. The curette is fabricated from a flexible material which is also transluscent to transmit light from a light source in the otoscope into the ear canal. An optical path is defined from the light source to illuminate tissues in the cavity. The light path and view path preferably converge so that a direct, illuminated view is provided to the examiner. The curette can have a channel for introducing medicinal fluids into the cavity or for withdrawing matter from the cavity. A swab for removal of fluids or culture samples from the ear canal can be provided on the curette. The head portion of the curette can have an inclined wall portion to provide a lens assembly for directing light from the curette into the cavity.

15 Claims, 3 Drawing Sheets

OTOSCOPE AND FLEXIBLE, DISPOSABLE CURETTE FOR USE THEREWITH

BACKGROUND OF THE INVENTION

The present invention pertains to an inexpensive, hand-held otoscope and a curette for use with the otoscope in examining small orifices in the body such as the ear canal. More particularly, the present invention pertains to both an otoscope having coupling means and a curette fabricated from a translucent, non-abrasive, flexible material, which curette is equipped with corresponding coupling means for releasably coupling it with the otoscope. The otoscope includes a light source, such that once coupled to the otoscope, the curette transmits the light from the source into the orifice so that both an optical path and a view path are provided into the orifice to enable examination and treatment without discomfort to the patient.

Often it is desirable to inspect the ear drum and the ear canal for evidence of infection, or for bulging which indicates undue pressure from the inner ear, or simply for wax which may plug the ear. Likewise, infected debris which accumulates as during "swimmer's ear" need also be examined for subsequent removal. In children, foreign material such as cotton, tissue paper, or even small toy beads, for example, may be found to occlude the ear canal and thus necessitate removal.

Practitioners such as an ear, nose and throat (ENT) specialists routinely have specialized equipment such as binocular microscopes, head mirrors providing illumination, suction devices, irrigation, and other special devices at their disposal. Such devices are quite expensive, however, and may further require special skills for their use. Consequently, most school nurses, or nurses in other care facilities are prevented from using such devices. Even many pediatricians and family practitioners either do not have such devices at their disposal or are not experienced enough in their use.

Without the benefit of the specialized equipment commonly available to ENT specialists, school nurses or pediatricians etc. frequently have carried out examinations of the ear canal with prior art otoscopes. Then if occluding matter was found, the ear would be irrigated with warm water and hydrogen peroxide, for example, by means of a syringe or other irrigation device to dissolve or soften the occluding material to permit the removal thereof. Once the matter, such as wax, is softened by the irrigation fluid, it would often be removed manually with the aid of a metal curette. An example of such a curette is provided in U.S. Pat. No. 2,331,732 which discloses a plastic handle, a shank part embedded in the handle and a head portion connected to the shank. The head portion is bowed to better fit the ear and comprises an eye formed of stiff wire bent back upon itself.

Examinations carried out in the foregoing manner using metal curettes could easily result in the abrasion of the tissues of the ear, especially when those tissues are wetted and softened by the irrigation fluid. Occasionally, even perforation of the ear drum can result. The risks involved in performing these procedures with equipment known in the art are even further increased when examining and treating small children. As is all too well known, children will cooperate minimally, if at all, and are likely to become fearful and move about during the examination. Moreover, due to the noise and sensation of the curette within the ear, some children may develop vertigo and nausea during examination or treatment. Thus, these procedures are made quite complicated by the child's movements, and much time is required to complete the examination and the treatment.

The problems inherent in examining sensitive orifices of the body have been recognized, and improved otoscopes and other ear cleaning devices have resulted. For example, U.S. Pat. No. 4,572,180 discloses a lighted ear canal curette instrument including a hand-held lighting member, a curette having an elongated handle and retaining members which telescopically receive both the handle member and the curette to secure the curette thereto. A magnification lens is hingedly attached to the lighting member to provide a view path as well as an optical path into the ear canal. U.S. Pat. Nos. 1,556,510; 3,110,304; 3,592,199; and 4,566,439 disclose other instruments for viewing into the ear canal or the like. Another hand-held curette is typified by U.S. Pat. No. 1,737,106, wherein an ear curette having a tubular handle and a stiff, but flexible non-metallic loop which projects from one end thereof is provided. A band of soft fabric forming a wiping element is secured at the opposite end of the handle. Various other curettes and sampling devices are disclosed in U.S. Pat. Nos. 622,386; 1,533,123; 3,254,356; 3,626,946; 3,635,222; and 4,027,658.

To most assuredly avoid injuring the tissues of the ear, especially the ears of small children during the inspection and cleaning thereof, excellent visual access should be provided. Further, any probing within the ear canal should be performed with a flexible member to prevent abrasion. This is especially important when the canal is made wet and particularly sensitive due to the softening effects of irrigating solutions or the like. Finally, the probing member should be disposable so as to ensure against contamination.

SUMMARY OF THE INVENTION

The present invention provides a flexible curette including coupling means for releasably coupling to an otoscope. The curette is comprised of a light-guiding material to conduct light from a source in the otoscope down along the length of the curette into the ear canal or other orifice so that both an optical path and a view path are provided into the ear. Due to the flexible, non-abrasive construction of the curette and the excellent view into the orifice afforded by the cooperating otoscope and curette, treatment and examination of the ear canal can be carried out with minimum discomfort and chance of injury to the patient.

The otoscope includes a light source housed within a cap having an opening through a front wall thereof to provide an optical path through the otoscope. The opening has coupling means therein for engaging with a curette. The curette of the present invention is constructed from a flexible material to have a base including corresponding coupling means, a head portion and a shaft which connects the base and the head portion. Due to the flexible nature of the curette, abrasion of ear tissue during the use is avoided. Moreover, the material making up the curette is preferably translucent for conducting light from the opening in the cap down along the shaft of the curette and through the head portion to illuminate the interior of the ear. Further still, the material of the curette is adapted to quickly assume ambient temperatures so as to further minimize discomfort during contact with the tissues in the ear.

Thus, an otoscope for use with a curette in accordance with the present invention in inspecting and treating small orifices, such as the ear, includes a tubular handpiece having a closed end and an open end. A light source is located in the open end and is positioned to provide illumination forwardly thereof. A cap having a forward end and a rear, open end telescopically fits over the open end of the handpiece and thus the light source. An opening through the front wall of the cap provides both coupling means for releasably coupling with a curette and a path for transmitting light through the otoscope. A frame carrying a lens is also disposed upon the cap and defines a view path for the examiner.

The curette according to the present invention includes a base, a head portion adapted to remove occluding matter from the ear canal, and a shank which connects the head portion to the base. At least the head portion and the shank are fabricated from a flexible material to prevent abrading or otherwise discomforting the ear during the use of the curette. Finally, corresponding coupling means are provided on the base of the curette to releasably couple with the otoscope. Since the material making up the curette is also transluscent to transmit light along the length thereof, attachment of the curette to the otoscope completes an optical path to illuminate the ear canal at the head portion of the curette.

In one particular form of the curette, a longitudinally extending channel is provided in the shank. Thus, in a preferred embodiment of the curette, the channel comprises a canal. This canal conducts fluids, introduced at the base, forwardly along the shank to the head portion where they are dispensed in the ear. Such a curette overcomes the problems of air bubbles in the ear which often form during dropper application of medicinal fluids.

Alternatively, in an embodiment in which the shank is tubular, the channel comprises an axial passageway therethrough, such passageway opening at about just above the head portion of the curette. At the base, the passageway through the shaft communicates with a radial passage opening at the base so that a suction passage is provided through the curette. Thus, for example, a suctioning device can be connected to the radial passage to suction the ear canal or, alternatively, fluid can be introduced into the suction passage to irrigate the ear canal.

Another form of the curette has a head portion comprising a spoon. A sock, woven from an absorbent material, covers the spoon to swab fluids or other matter from the ear.

In still another form of the curette of the present invention, the head portion includes an eyelet portion and an inclined wall portion connecting the eyelet portion to the shank. The inclined wall portion serves as a lens to direct light transmitted from the otoscope, through the curette, into the cavity.

BRIEF DESCRIPTION OF THE DRAWINGS

These and other aspects of the present invention are more apparent from the following detailed description and claims, particularly when considered in conjunction with the accompanying drawings in which like parts bear like reference numerals. In the drawings:

FIG. 8 is an enlarged, partial view of still another embodiment of a curette in accordance with the present invention.

DESCRIPTION OF THE PREFERRED EMBODIMENT

Figure 1:
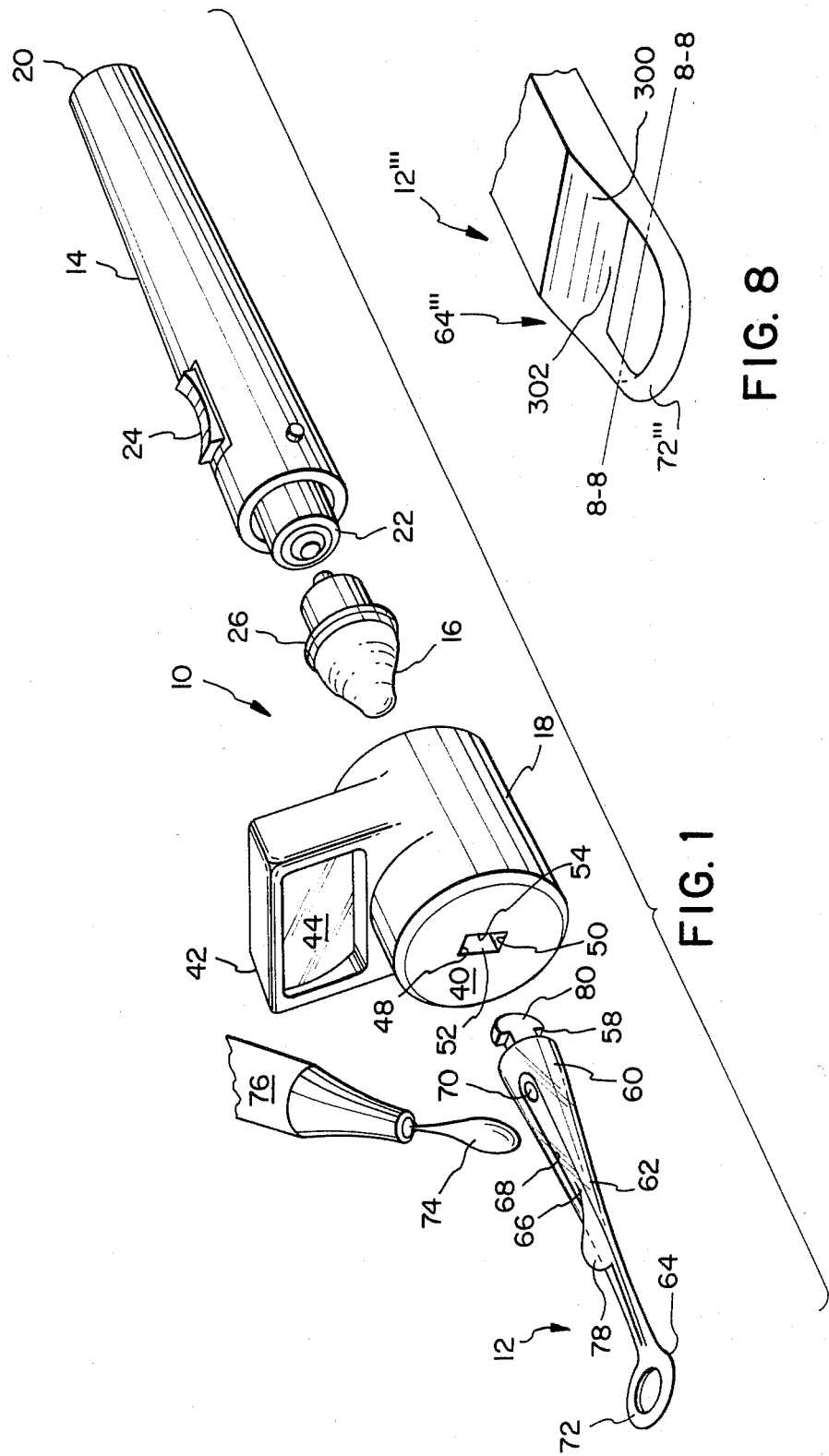
FIG. 1 is an exploded perspective view showing an otoscope including coupling means and a curette having corresponding coupling means for engaging the otoscope in accordance with the present invention.

FIG. 1 is an enlarged perspective view of a preferred embodiment of an otoscope generally designated as 10 with a curette 12 ideally suited for use with the otoscope invention. Preferably, otoscope 10 is constructed from a rigid, plastic material for inexpensive and simple manufacture. Otoscope 10 and curette 12 are constructed to provide means for probing and examining small orifices in the body, such as the ear canal.

As seen in FIG. 1, otoscope 10 includes a handpiece 14, an illuminating lamp 16 and a cap 18. Handpiece 14 is tubular and has a closed end 20 to provide a cavity for receiving one or more batteries 22 to power lamp 16. On/off switch 24 controls a circuit between batteries 22 and lamp 16.

Figure 2:
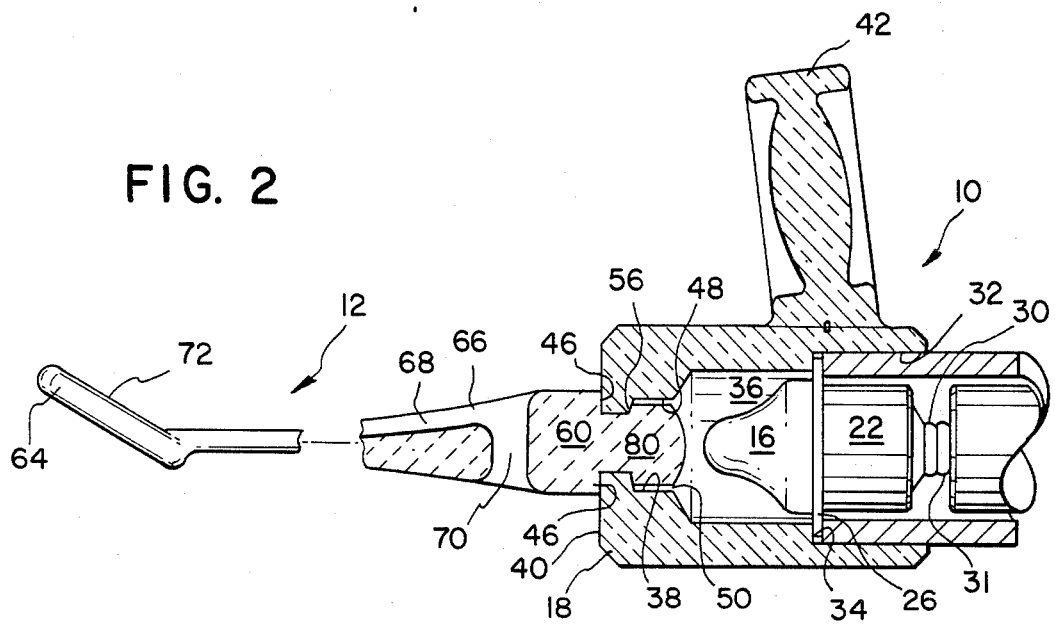
FIG. 2 is a cut-away, partial side view of the otoscope and curette of FIG. 1.

As can best be seen from FIG. 2, lamp 16 has an annular flange 26 which engages against the open end of handpiece 14. In this way, contacts 30 and 31 of lamp 16 and battery 22, respectively, positively engage one another.

Cap 18 (FIG. 2) telescopically fits over the open end of handpiece 14 to enclose lamp 16 and batteries 22 within the handpiece. Thus, as shown in cut-away view in FIG. 2, cap 18 has a large diameter section 32 bordered by shoulder 34 upon which flange 26 of lamp 16 abuts. Section 32 communicates with an intermediate section 36 of smaller diameter, which receives lamp 16. Intermediate section 36 in turn narrows to form an opening 38 through front wall 40 of cap 18. Intermediate section 36 and opening 38 thus provide a light transmission path from lamp 16 through cap 18.

Referring to FIG. 1, frame 42 is attached to cap 18 to provide a view path along otoscope 10 and curette 12 to enable the physician to view into the cavity, such as the ear canal. A lens 44 is mounted within frame 42. Lens 44 is of the magnifying type, and preferably is a 2-3 power lens. Alternatively, lens 44 could have greater or lesser magnifying power according to the needs of the examiner.

In the embodiment of FIGS. 1 and 2, frame 42 is integrally formed with cap 18. Alternatively, as shown in FIGS. 3 and 4, frame 42 can be pivotally attached to cap 18 so that the lens 44 can be pivoted out of the line of sight to suit the examiner.

Figure 3:
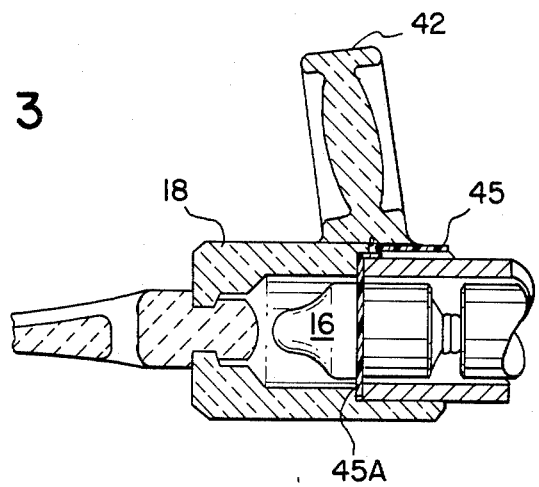
FIGS. 3 and 4 are cut-away, sectional views showing a modified switch and lens frame arrangement for the otoscope of FIGS. 1 and 2.
Figure 4:
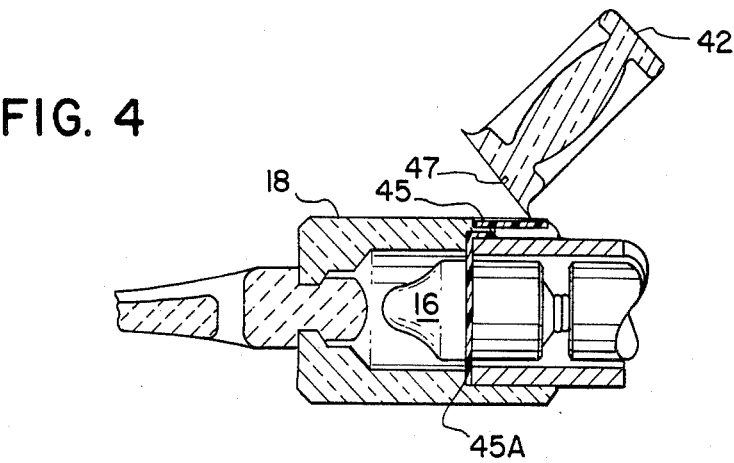

Frame 42 is movable in the embodiments of FIGS. 3 and 4 from a first position shown in FIG. 4 to a second position shown in FIG. 3 whereby an electrical circuit between batteries 22 and lamp 16 is completed and the lamp is energized. Thus, in the embodiment illustrated in FIGS. 3 and 4, a flange 47 on frame 42 depresses contact 45 into conductive association with a like contact 45A of lamp 16. Frame 42 constitutes the on/off switch for the otoscope, and on/off switch 24 on handpiece 14 can be omitted.

With further reference to FIGS. 1 and 2, opposing flanges 46 extend inwardly of top and bottom walls 48 and 50 of opening 38. Opening 38 also has sidewalls 52 and 54. Walls 52 and 54 and inwardly extending flanges 46 together constitute coupling means hereinafter generally referred to by numeral 56. Coupling means 56 is constructed to connect with corresponding coupling means 58 on curette 12.

In a preferred curette shown in FIG. 1, coupling means 58 is integrally connected to base 60. Base 60 tapers to form an elongated shank 62 which at its free end terminates in head portion 64. Curette 12 preferably is constructed entirely from a flexible plastic material. So constructed, base 60 due to its large diameter, will be relatively inflexible, while shank 62 and head portion 64 will be relatively flexible to avoid abrading the tissues of the ear. More preferably, the material making up curette 12 is also of a type that avoids a feeling of cold when head portion 64 initially contacts the tissues of the ear. Finally, the curette is comprised of a material capable of functioning as a light guide to complete an optical path from lamp 16, through the curette, into the ear or other orifice. Curette 12 can be fabricated from any well known light emitting material whereby the light from lamp 16 is conducted along curette 12 to emerge at head portion 64 to illuminate the orifice. Ideally, the view path formed along otoscope 10 by lens frame 42 holding lens 44 converges with the optical path to provide a direct, unobstructed view of the illuminated interior of the ear canal.

Curette 12 in FIG. 1 also has a channel 66 extending longitudinally thereof along shank 62. Channel 66 comprises a canal 68 along the upper surface of shank 62. Canal 68 begins at base 60 at about just where base 60 begins to taper to form shank 62. At base 60, canal 68 progresses from its intersection with a drain opening 70 along shank 62 to terminate at head portion 64.

In preferred curette 12, head portion 64 further comprises an annular eyelet 72. Alternatively, eyelet 72 could be of any other shape suitable for probing the ear canal and removing cerumen or the like from the cavity. Eyelet 72 is turned upwardly at an angle with respect to shank 62. So upturned, eyelet 72 is particularly suited to removing foreign matter or accumulated wax from within the ear. Further, since eyelet 72, like the remainder of curette 12, is constructed from the flexible, non-abrasive material, discomfort to the ear drum is minimized.

FIG. 1 particularly illustrates one of several advantages deriving from curette 12 having canal 68, drain 70 and eyelet 72. As seen in FIG. 1, fluid 74 may be dispensed from a fluid dispenser 76 to form droplets 78 conducted along canal 68 and into the body cavity. In this way, curette 12 is especially equipped to deliver a fluid, such as medicine to the ear canal or to the ear drum while avoiding the problem of air bubbles which often form when administering medicines by dropper or pipette. Formation of air bubbles is prevented since the fluid from curette 12 comes into immediate contact with the tissues to be treated. Any excess fluid 74 introduced into canal 68 can be discharged from the curette through drain opening 70 and thereby control the amount of fluid conducted into the ear.

With regard to the interconnection of curette 12 and otoscope 10, coupling means 56 located in cap 18 engages corresponding coupling means 58 to removably mount curette 12 to cap 18. Coupling means 58 of curette 12 includes a tongue 80 which is received within opening 38 and locked therein by engagement with flanges 46. Since tongue 80 is constructed from the same flexible material making up the remainder of curette 12, tongue 80 may be disengaged from flanges 46 by pulling curette 12 outwardly from cap 18 as by hand. Thus curette 12 is removable and can be disposed after use. It is seen that each of successive examinations with otoscope 10 can then be performed with a new, sterile curette.

Alternatively, tongue 80 can be rigid and flanges 46 flexible. Also, both tongue 80 and flanges 46 can be flexible as is apparent to those skilled in the art.

Figure 5:
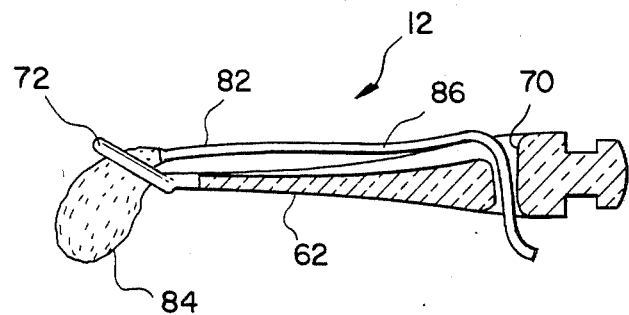
FIG. 5 is a cut-away, side elevation view of the curette of FIGS. 1 and 2 in conjuncton with swab means for collecting fluids from within the ear.

In FIG. 5, curette 12 is shown in conjunction with swab means 82 for absorbing fluids or the like from the ear. Swab means 82 includes a swab end 84 connected to a cord or wire 86. Cord or wire 86 is laced through eyelet 72 and longitudinally extends along shank 62. Conveniently, cord or wire 86 is also laced through drain opening 70 as shown so that it is relatively constrained and can be easily grasped. Swab end 84 is held within eyelet 72 where it is positioned to "mop up" or absorb fluids within the ear. Accordingly, swab means 82 provides an excellent device for collecting a pure culture sample from the drainage fluids of the ear.

Figure 6:
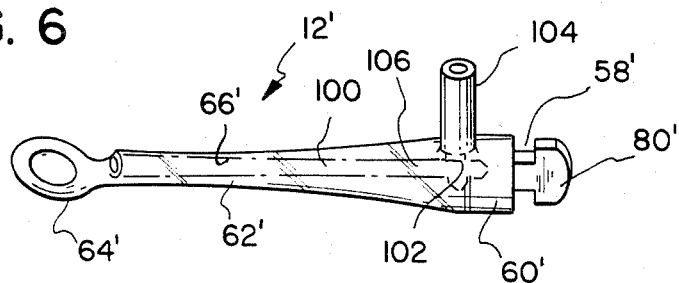
FIG. 6 is a perspective view of a first alternative embodiment of a curette in accordance with the invention.

A first alternative embodiment of a curette 12' is shown in FIG. 6. Curette 12' likewise includes a base 60', a shank 62' and a head portion 64'. Curette 12' includes coupling means 58' likewise including a tongue 80'. Curette 12' removably attaches the preferred otoscope 10 in the previously described manner.

Curette 12' differs from curette 12 in that shank 62' is tubular. That is, channel 66' of shank 62' is an elongated passage 100 which extends longitudinally through the shank. At base 60', passage 100 communicates with a radial passage 102. Nozzle 104 is mounted upon base 60' at about the junction of the base 60' and shank 62'. Nozzle 104 is tubular and communicates with radial passage 102 which in turn communicates with elongated passage 100. At its other end, passage 100 opens proximate head portion 64'. Curette 12', having communicating passages 100 and 102 and nozzle 104 thus provides a suction passage, hereinafter referred to as 106, into the body cavity. A suctioning device (not shown) can be connected at nozzle 104 and when head portion 64' is inserted into the ear, fluid or the like may be aspirated directly from the ear through suction passage 106. Alternatively, suction passage 106 can be used to deliver medicinal fluids into the ear or to irrigate the ear. Irrigation can be carried out, for example, by connecting a fluid conduit to nozzle 104 and introducing irrigation fluid through passage 106.

Figure 7:
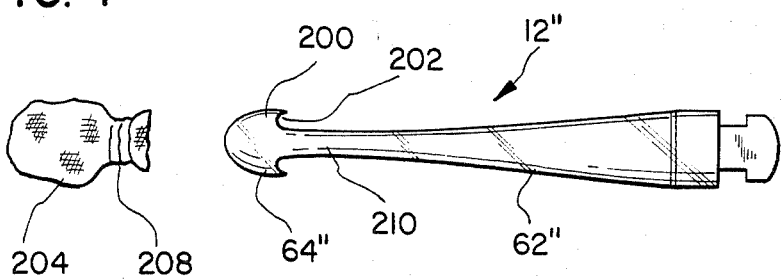
FIG. 7 is another embodiment of a curette in accordance with the invention.

FIG. 7 shows still another embodiment of a curette 12". Rather than having the eyelet 64 or 64', head portion 64" of curette 12" in FIG. 7 comprises a spoon 200. Spoon 200 likewise is slightly upturned with respect to shank 62" of curette 12". Otherwise, spoon 200 is flat and has side flanges 202 for securing absorbent sock 204 thereover. Sock 204 is made from cotton or a similar sterile absorbent material. Sock 204 has an enlarged portion for telescopically covering spoon 200 and an elastic portion 208. Elastic portion 208 expands to fit over spoon 200 and then contracts around neck 210 of shank 62". Curette 12" having spoon 200 covered by absorbent sock 204 provides means for absorbing fluids from within the ear or for obtaining fluid samples from the ear. Spoon 200 likewise can be used to remove foreign matter from the ear, and in this regard the spoon can be used with or without sock 204 depending on the material to be removed.

FIG. 8 is an enlarged, partial view of the head portion 64''' and the shank 62''' of yet another embodiment of a curette 12''' according to the present invention. Head portion 64''' comprises eyelet portion 72''' and inclined wall portion 300 connecting the eyelet portion to shank 62'''. Inclined wall portion 300 tapers from shank 62''' to eyelet portion 72'''. As is evident, eyelet portion 72''', inclined wall portion 300, and shank 62'', could be integral or otherwise secured to one another. Indeed, in an integral arrangement as shown in FIG. 8 where eyelet portion 72''' has a cross-sectional width along line 8—8 that is either equal to or less than that of shank 62''', the manufacture of curette 12''' by injection molding is simplified since the mold for forming the curette would not require frequent maintenance to prevent the formation of a sharp edge or "flash" on the eyelet portion. Alternatively, the eyelet portion could be of larger size or be circular rather than have the shape shown in FIG. 8.

Curette 12''' is likewise constructed from a flexible, transluscent material for transmitting light into the cavity to be probed. Inclined wall portion 300, so configured, thus provides lens means 302 for directing light, emerging from the wall portion into the cavity. Eyelet portion itself would further provide means for illuminating the cavity since preferably, it too would be constructed from the transluscent material. Preferred curette 12 would also comprise a base (not shown) for securing the curette to an otoscope according to the present invention and could further comprise a channel (not shown) providing either a fluid canal or a suction passage into the cavity.

So constructed, any of curettes 12, 12', 12'' or 12''' having corresponding coupling means easily and removably attach to otoscope 10 having coupling means 56. Thus, curettes 12, 12', 12'', and 12''' are disposable. After their use in probing and treating infected ear tissues, the contaminated curettes are simply detached from otoscope 10 and discarded. Indeed, routine cleaning of otoscope 10 is facilitated before attachment of a new sterile curette.

Frame 42 mounts lens 44 in a position to provide a view path through lens 44 into the orifice. Thus, lens 44 is mounted so that the examiner's own fingers do not block his path of vision Preferably, this view path converges at about the head portion of the curette with the optical transmission path defined along the length of the curette to provide a direct, illuminated view of the interior tissues of the ear canal. This excellent view, in conjunction with the flexible, non-abrasive construction of the curette according to the present invention results in apparatus for examining and treating very sensitive orifices, such as the ear canal, with minimum discomfort to a patient. Thus, examination and treatment procedures are made safer and more efficient.

Although the present invention has been described with reference to the preferred embodiments, numerous modifications, rearrangements and substitutions could be made, and the resulting devices would still remain well within the scope of the invention.

What is claimed is:

1. In combination with a curette fabricated from a light-guiding, flexible material, wherein said curette has a base, a head portion and a shank that connects said base and said head portion, said base including coupling means extending in opposition to said shank, an otoscope for examining a small cavity in the body, said otoscope comprising:
   a tubular handle portion having a closed end and an open end;
   a lamp located in said handle portion and being connectable to a power source for providing illumination forwardly thereof;
   a cap including a front wall and a rear, open end, said rear, open end telescopically fitting over said lamp and said open end of said handle portion in enclosing relationship thereto, said front wall having an opening therein;
   coupling means located in said opening for receiving said corresponding coupling means on said curette; whereby said open end of said cap, said opening through said front wall and said light-guiding material in said curette define an optical path from said lamp to within the cavity; and
   lens means disposed on said cap, said means providing a view path longitudinally of said otoscope and said curette.

2. The combination as claimed in claim 1, wherein said optical path and said view path converge along said shank and said head portion of said curette.

3. The combination as claimed in claim 2, wherein said corresponding coupling means on said base of said curette comprises a tongue; said coupling means in the cap comprises inwardly extending flanges; and said tongue engages said flanges to releasably secure said curette to said front wall of said cap.

4. A curette adapted for use with an otoscope in probing a small cavity in the body and removing matter therefrom without substantial discomfort to sensitive areas within the cavity, said curette being fabricated from a translucent flexible material and comprising:
   a base;
   an upturned head portion, said head portion comprising a spoon
   a shank connecting saisd head portion to said base; and
   coupling means located on said base and extending from said base in a direction opposite said shank for coupling said curette with an otoscope, said curette defining an optical path for transmitting light provided at said coupling means, through said base and said shank to illuminate said head portion and the cavity.

5. A curette as claimed in claim 4, further comprising an absorbent sock, said sock telescopically fitting over said spoon.

6. A currette adapted for use with an otoscope in probing a small cavity in the body and removing matter therefrom without substantial discomfort to sensitive areas within the cavity, said curette being fabricated from a translucent flexible material and comprising:
   a base;
   an upturned head portion;
   a shank connecting said head portion to said base, said shank having a longitudinally extending canal in an upper surface of said shank for conducting fluids introduced near said base forwardly along said shank to said head portion; and coupling means located on said base and extending from said base in a direction opposite said shank for coupling said curette with an otoscope, said curette defining an optical path for transmitting light provided at said coupling means, through said base and said shank to illuminate said head portion and the cavity.

7. A curette as claimed in claim 6, wherein said base has a transverse drain opening therein.

8. In combination with the curette as claimed in claim 7, swab means including a swab connected to cord, said cord extending through said eyelet and said drain opening, said swab being held within said eyelet.

9. A curette adapted for use with an otoscope in probing a small cavity in the body and removing matter therefrom without substantial discomfort to sensitive areas within the cavity, said curette being fabricated from a translucent flexible material and comprising:
   a base;
   an upturned head portion;
   a shank connecting said head portion to said base, said shank having a passageway extending longitudinally through said shank, said pasageway opening proximate said eyelet and communicating with a radial passage opening near said base, said curette further comprising a nozzle, said radial passage and said longitudinal passage defining a suctioning passage through said curette for suctioning debris from the cavity; and
   coupling means located on said base and extending from said base in a direction opposite said shank for coupling said curette with an otoscope, said curette defining an optical path for transmitting light provided at said coupling means through said base and said shank to illuminate said head portion and the cavity.

10. A curette as claimed in claims 6 or 9, wherein said head portion comprises an eyelet, said eyelet having a cross-sectional width smaller than the width of said shank.

11. A curette adapted for use with an otoscope in probing a small cavity in the body and removing matter therefrom without substantial discomfort to sensitive areas within the cavity, said curette being fabricated from a transluscent flexible material and comprising:
   a base;
   an upturned head portion;
   a shank connecting said head portion to said base; and
   coupling means located on said base and extending from said base in a direction opposite said shank for coupling said curette with an otsocope, said curette defining a light transmission path through said base and said shank to illuminate said head portion and the cavity, said head portion further comprising an eyelet portion and an inclined wall portion connecting said eyelet portion to said shank, said inclined wall portion tapering from said shank to said eyelet portion and defining lens means for directing light into the cavity.

12. A curette as claimed in claim 11 wherein said eyelet portion is circular.

13. A curette as claimed in claim 11 wherein said eyelet portion has a cross-sectional width smaller than the width of said shank.

14. A currette as claimed in claim 11 wherein said coupling means comprises a tongue extending from said base in a direction opposite to said shank.

15. A curette as claimed in claims 4, 6, 9, or 11, wherein said coupling means comprises a tongue.

* * * * *